United States Patent [19]

Kitahara et al.

[11] Patent Number: 4,494,374
[45] Date of Patent: Jan. 22, 1985

[54] AIR/FUEL RATIO MONITORING SYSTEM IN IC ENGINE USING OXYGEN SENSOR

[75] Inventors: Tsuyoshi Kitahara, Yokohama; Kohki Sone, Tokyo; Masaaki Uchida, Yokosuka, all of Japan

[73] Assignee: Nissan Motor Co., Ltd., Yokohama City, Japan

[21] Appl. No.: 461,475

[22] Filed: Jan. 27, 1983

[30] Foreign Application Priority Data

Jan. 29, 1982 [JP] Japan .................. 57-12642

[51] Int. Cl.³ .............................. F01N 3/20
[52] U.S. Cl. ..................... 60/276; 123/440; 123/489; 123/589
[58] Field of Search .............. 60/276; 123/440, 589, 123/489

[56] References Cited

U.S. PATENT DOCUMENTS

| 4,167,925 | 9/1979 | Hosaka | 60/276 |
| 4,170,965 | 10/1979 | Aono | 123/440 |
| 4,354,468 | 10/1982 | Sone | 123/440 |
| 4,391,256 | 7/1983 | Sawada | 60/276 |
| 4,392,471 | 7/1983 | Miyagi | 123/440 |

Primary Examiner—Douglas Hart
Attorney, Agent, or Firm—Schwartz. Jeffery, Schwaab, Mack, Blumenthal & Koch

[57] ABSTRACT

An air/fuel ratio monitoring system in an IC engine, using an oxygen sensor of the concentration cell type which has a laminate comprising an inner electrode layer, a microscopically porous layer of oxygen ion conductive solid electrolyte and an outer electrode layer exposable to exhaust gas and which exhibits a sharp change in output voltage level in response to a change in the air/fuel ratio in the engine across a stoichiometric ratio. To ensure accurate monitoring of the air/fuel ratio even when the engine is operated under conditions which cause a large rise or fall in an average level of the output of the oxygen sensor, the monitoring system has a signal treatment means for producing a variable reference voltage, with which the sensor output is compared, by first adding a definite voltage to or subtracting a definite voltage from the output of the oxygen sensor depending on the result of comparison between the sensor output and the reference voltage and then smoothing the voltage resulting from the addition or subtraction of the definite voltage.

5 Claims, 10 Drawing Figures

AIR/FUEL RATIO MONITORING SYSTEM IN IC ENGINE USING OXYGEN SENSOR

BACKGROUND OF THE INVENTION

This invention relates to a system for monitoring the air/fuel ratio in an internal combustion engine by using an oxygen sensor of the concentration cell type in the exhaust gas.

In recent internal combustion engines and particularly in automotive engines, it is conventional to control the air/fuel mixing ratio precisely to a predetermined optimum value by performing feedback control. In many cases the target value of the air/fuel ratio under feedback control is a stoichiometric air/fuel ratio. For example, when a so-called three-way catalyst is used in the exhaust system to achieve reduction of NOx and oxidation of CO and HC simultaneously, the air/fuel ratio must be controlled precisely to a stoichiometric ratio because this catalyst exhibits optimum conversion efficiencies in an exhaust gas produced by combustion of a stoichiometric air-fuel mixture.

In current feedback control systems, it is usual to produce a feedback signal indicative of the air/fuel ratio of an air-fuel mixture actually supplied to the engine by sensing the concentration of oxygen in the exhaust gas since there is a determined relationship between the air/fuel ratio in the engine and the oxygen content in the exhaust gas.

As for the device to sense the oxygen concentration in the exhaust gas to thereby monitor the air/fuel ratio in the engine, it is usual to use an oxygen sensor of the concentration cell type having a layer of an oxygen ion conductive solid electrolyte such as zirconia stabilized by calcia or yttria and two electrode layers formed on the outer and inner surfaces of the solid electrolyte layer, respectively. An oxygen sensor of this type generates an electromotive force where there is a difference between the partial pressure of oxygen in the exhaust gas to which the outer electrode layer is exposed and an oxygen partial pressure at the inner electrode layer.

In this field, a recent trend is to miniaturize the oxygen sensor by constructing it as a laminate of thin, film-like layers on a plate-shaped ceramic substrate of very small size and by devising a certain method for producing an oxygen partial pressure of suitable level at the inner electrode layer of the sensor without using an external oxygen source material such as air. In an oxygen sensor of this category the solid electrolyte layer is made microscopically porous and permeable to gas molecules. When this oxygen sensor is disposed in the exhaust gas, an oxygen partial pressure nearly equal to the oxygen partial pressure in the exhaust gas always acts on the outer electrode layer. Furthermore, an oxygen partial pressure is produced at the inner electrode layer too by reason of inward diffusion of the exhaust gas containing some oxygen through the porous solid electrolyte layer. However, the oxygen partial pressure at the inner electrode layer is not always equal to the oxygen partial pressure at the outer electrode layer because the solid electrolyte layer is relatively low in its porosity and, hence, offers some resistance to the diffusion of exhaust gas or oxygen molecules therethrough. Therefore, when a considerable change is produced in the concentration of oxygen in the exhaust gas by a change in the air/fuel ratio in the engine across the stoichiometric ratio, a great difference arises between the oxygen partial pressure at the outer electrode layer of the oxygen sensor and that at the inner electrode layer, so that the output voltage of the oxygen sensor exhibits a sharp change from a high level to a low level, or reversely. Such a change in the output voltage of the oxygen sensor can easily be detected by continuously comparing the output voltage of the oxygen sensor with a suitably predetermined reference voltage. Accordingly an oxygen sensor of this type is suitable for use in a feedback control system aiming at a stoichiometric air/fuel ratio in an internal combustion engine.

However, the accuracy of monitoring of the air/fuel ratio by the above described method is not guaranteed when the engine is not operated in a steady state. For example, during operation of the engine under transitional operating conditions, during acceleration with temporarily increased feed of fuel or during temporary cutoff of the fuel feed, there occurs a considerable rise or fall in an average level of the output voltage of the oxygen sensor, whereas the aforementioned reference voltage remains unchanged. Then there arises a possibility that a change in the actual air/fuel ratio across the stoichiometric ratio does not cause the output voltage of the oxygen sensor to intersect the reference voltage, so that the air/fuel ratio is misjudged.

SUMMARY OF THE INVENTION

It is an object of the present invention to provide an improved system for monitoring the air/fuel ratio in an internal combustion engine as the basis of feedback control of the air/fuel ratio by using an oxygen sensor of the above described concentration cell type which is responsive, when disposed in the exhaust gas of the engine, to a change in the air/fuel ratio across the stoichiometric ratio. The system can continue accurate monitoring of the air/fuel ratio even when the engine is operated under such conditions as cause a considerable rise or fall in an average level of the output voltage of the oxygen sensor.

An air/fuel ratio monitoring system according to the invention has an oxygen sensor of the concentration cell type disposed in an exhaust passage of the engine, the oxygen sensor having a laminate of an inner electrode layer, a microscopically porous layer of an oxygen ion conductive solid electrolyte and an outer electrode layer, exposed to exhaust gas for producing an output which varies between a high-level voltage signal when the air/fuel ratio is below the stoichiometric ratio of air-fuel mixture supplied to the engine to a low-level voltage signal when the air/fuel ratio is above the stoichiometric ratio, and judgement means for producing an air/fuel ratio signal which indicates whether the air/fuel ratio is above or below the stoichiometric ratio by comparing the output of the oxygen sensor with a reference voltage. According to the invention, the air/fuel ratio monitoring system comprises a modulating means for producing a modulated voltage signal by subtracting a first definite voltage from the output of the oxygen sensor when the air/fuel ratio signal indicates that the air/fuel ratio is below the stoichiometric ratio but by adding a second definite voltage to the output of the oxygen sensor when the air/fuel ratio signal indicates that the air/fuel ratio is above the stoichiometric ratio, and smoothing means for smoothing the modulated voltage signal to produce a smoothed voltage and supplying the smoothed voltage to the judgement means as the aforementioned reference voltage.

In the system according to the invention, the reference voltage is automatically varied so as to rise and fall as the level of the output voltage of the oxygen sensor rises and falls. Accordingly a comparison between the sensor output voltage and the reference voltage can surely be achieved and, hence accurate judgement of the air/fuel ratio can be made even when an average level of the sensor output voltage undergoes a considerable change depending on the operating conditions of the engine.

DETAILED DESCRIPTION OF THE INVENTION

Figure 1:
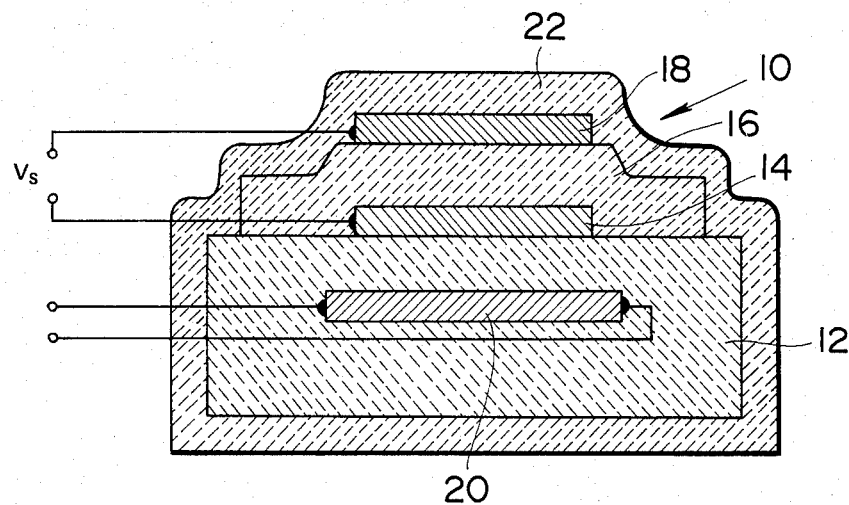
FIG. 1 is a cross-sectional view of an oxygen sensor used in the present invention.

FIG. 1 shows an exemplary construction of an oxygen sensor 10 used in the present invention. A structurally basic member of this sensor 10 is a plate-shaped substrate 12 made of a ceramic material such as alumina.

The sensitive part of the oxygen sensor 10 takes the form of a laminate of thin layers, which can be formed by the conventional thick-film technique, supported on the ceramic substrate 12. The laminate consists of an inner electrode layer 14, which is often called reference electrode layer, laid on the upper surface of the substrate 12, a layer 16 of an oxygen ion conductive solid electrolyte such as zirconia containing a small amount of stabilizing oxide such as yttria or calcia formed on the inner electrode layer 14 so as to substantially entirely cover the electrode layer 14, and an outer electrode layer 18, which is often called measurement electrode layer, laid on the upper surface of the solid electrolyte layer 16. The outer electrode layer 18 and the solid electrolyte layer 16 are microscopically porous and permeable to gas molecules. Platinum is a typical material for the outer and inner electrode layers 18 and 14. The thus constructed laminate has a total thickness of about 70 microns for example. A heater 20 in the form of either a thin layer or a thin wire of a suitable metal such as platinum is embedded in the ceramic substrate 12 because the solid electrolyte 16 hardly exhibits its activity at relatively low temperatures such as below about 400° C. The outer surfaces of the oxygen sensor 10 are coated with a porous protective layer 22 formed of a ceramic material.

Figure 2:
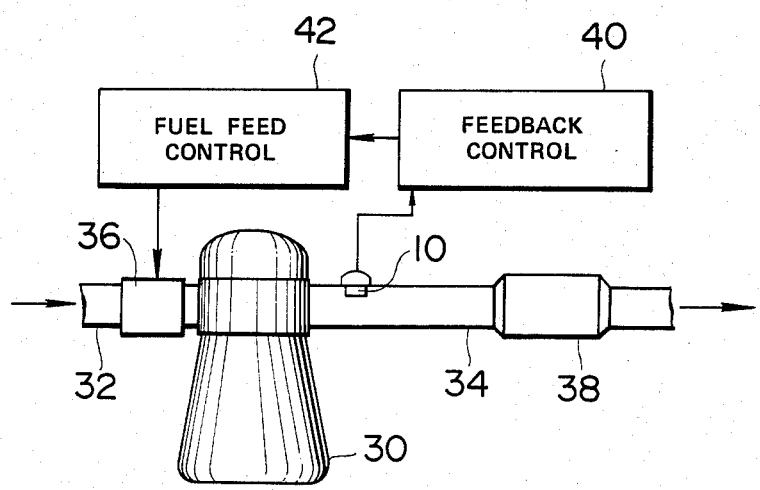
FIG. 2 is a diagrammatic presentation of an internal combustion engine system including an air/fuel ratio monitoring system according to the invention.

In FIG. 2, reference numeral 30 indicates an automotive internal combustion engine provided with an induction passage 32 and an exhaust passage 34. Indicated at 36 is an electrically controlled fuel-supplying apparatus such as electronically controlled fuel injection valves. A catalytic converter 38 that occupies a section of the exhaust passage 34 contains a conventional three-way catalyst for example.

To perform feedback control of the fuel-supplying apparatus 36 with the aim of supplying an optimum air-fuel mixture, in this case a stoichiometric mixture, to the engine 30 during its normal operation for thereby allowing the catalyst in the converter 38 to exhibit its optimum conversion efficiencies, the oxygen sensor 10 of FIG. 1 is disposed in the exhaust passage 34 at a section upstream of the catalytic converter 38. The oxygen sensor 10 serves as a probe to detect deviations of actual air/fuel ratio in the engine 30 from the intended stoichiometric air/fuel ratio by sensing changes in the concentration of oxygen in the exhaust gas.

An electronic control unit 40 receives the output of the oxygen sensor 10 and provides a control signal to a control or drive element 42 of the fuel-supplying apparatus 36 based on the deviations of the actual air/fuel ratio indicated by the output of the oxygen sensor 10 from the desired air/fuel ratio represented by a reference signal. The present invention is primarily concerned with this control unit 40.

The oxygen sensor 10 of FIG. 1 operates on the principle of oxygen concentration cell. In the exhaust passage 34 in the engine system of FIG. 2, the exhaust gas easily permeates through the porous protective layer 22 of the oxygen sensor 10 and arrives at the outer electrode layer 18 of the sensor 10. Then a portion of the exhaust gas further diffuses inward through the micropores in the solid electrolyte layer 16, but the exhaust gas takes some time to arrive at the inner electrode layer 14 across the solid electrolyte layer 16 because of relatively low porosity of the solid electrolyte layer 16 compared with the protective coating layer 22.

Figure 3:
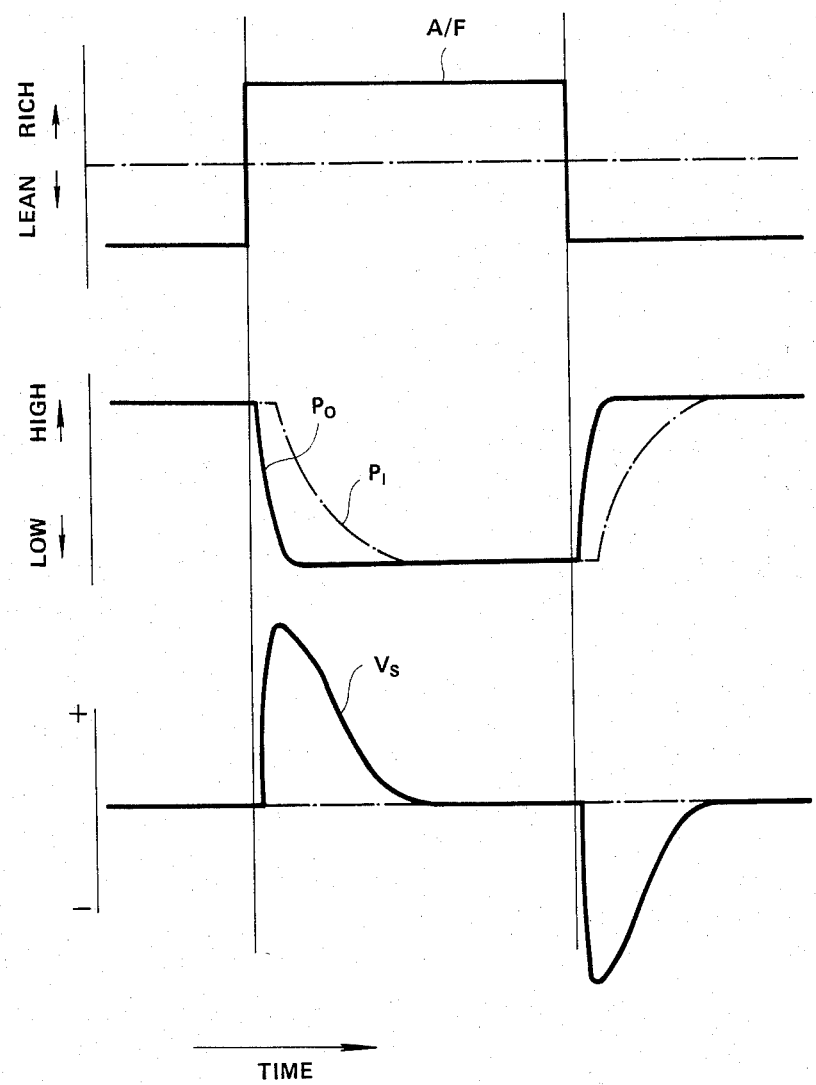
FIG. 3 is a timing chart showing the functioning of the oxygen sensor of FIG. 1 disposed in exhaust gases of an internal combustion engine.

Referring to FIG. 3, the actual air/fuel ratio or the content of fuel in the air-fuel mixture supplied to the engine 30 will periodically vary in the manner as represented by curve A/F since the air/fuel ratio is under feedback control with the aim of a stoichiometric air/fuel ratio. When the air/fuel ratio in the engine 30 shifts from the lean side to the fuel-rich side across the stoichiometric ratio, there occurs a sharp decrease in the oxygen partial pressure in the exhaust gas. Since the protective layer 22 of the oxygen sensor 10 is high in porosity, an oxygen partial pressure $P_O$ at the outer electrode layer 18 of the sensor 10 undergoes a sharp decrease nearly tracking the oxygen partial pressure in the exhaust gas flowing around the sensor 10. However, an oxygen partial pressure $P_I$ at the inner electrode layer 14 undergoes a considerably slower decrease by reason of the relatively low rate of diffusion of exhaust gas or oxygen molecules through the solid electrolyte layer 16 which is lower in porosity than the outer protective layer 22. Accordingly a difference arises between the oxygen partial pressure $P_O$ at the outer electrode layer 18 and the oxygen partial pressure $P_I$ at the inner electrode layer 14, and therefore the oxygen sensor 10 generates an electromotive force $V_S$ across its solid electrolyte layer 16. The magnitude of this electromotive force $V_S$ is given by the Nernst's equation:

$$V_S = (RT/4F)\log_e(P_O/P_I)$$

where R is the gas constant, F is the Faraday constant, and T represents absolute temperature.

An output voltage of the oxygen sensor 10 measured between the inner and outer electrodes 14 and 18 can be taken as approximately equal to the electromotive force $V_S$. As shown in FIG. 3, the output voltage $V_S$ of the oxygen sensor 10 exhibits a sharp rise to the positive side in response to a change in the air/fuel ratio in the engine across the stoichiometric ratio from the lean side to the fuel-rich side and a sharp lowering to the negative side in response to a reverse change in the air/fuel ratio.

In the oxygen sensor 10 in FIG. 2, the oxygen partial pressure $P_O$ acting on the outer electrode layer 18 is always nearly equal to a variable oxygen partial pressure in the exhaust gas, whereas the oxygen partial pressure $P_I$ acting on the inner electrode layer 14 is regarded as a mean partial pressure of oxygen in the exhaust gas with respect to time, and the output voltage $V_S$ of the oxygen sensor 10 represents a difference between the two oxygen partial pressures $P_O$ and $P_I$.

Figure 4:
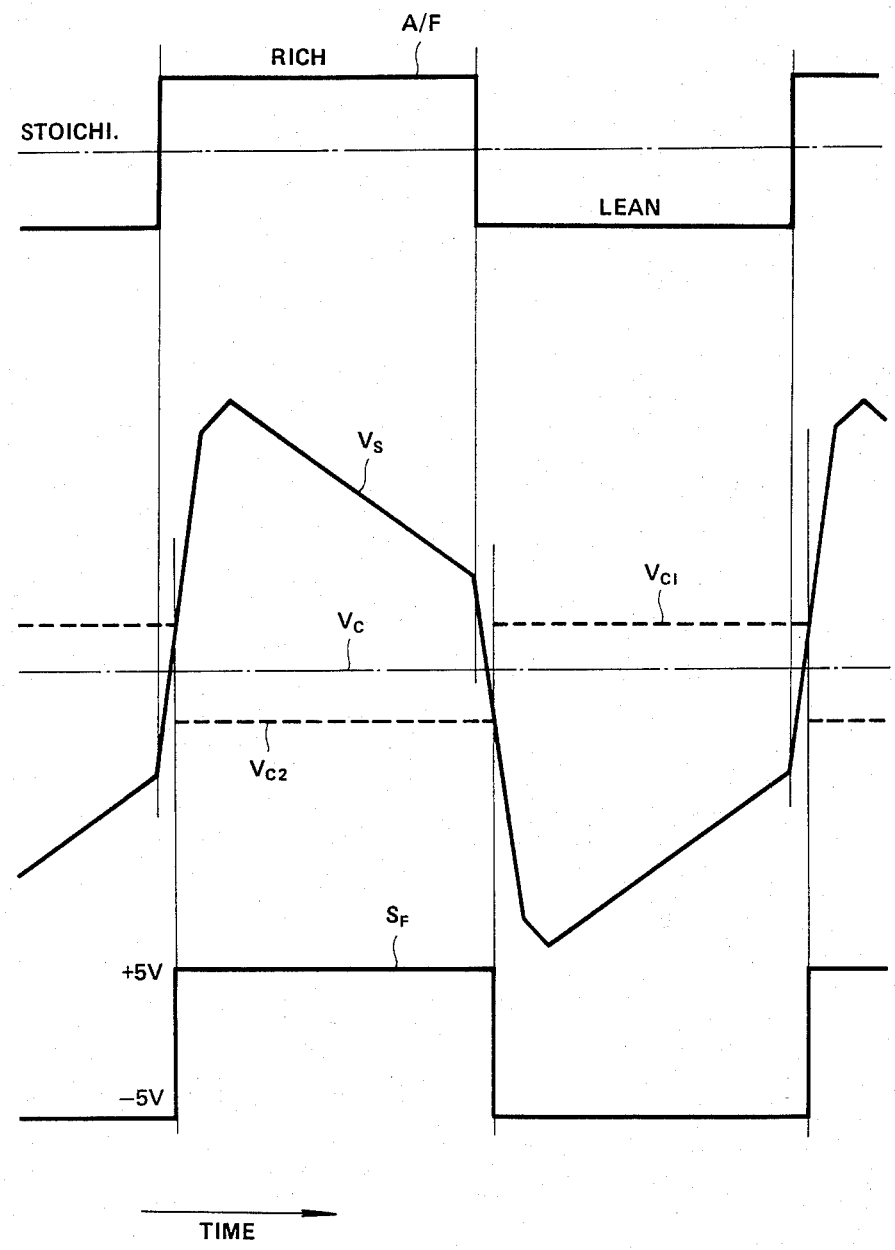
FIG. 4 is a chart showing the manner of producing an air/fuel ratio signal in a heretofore proposed system using the oxygen sensor of FIG. 1.

FIG. 4 shows the manner of producing an air/fuel ratio signal $S_F$ by using the output $V_S$ of the oxygen sensor 10 in a heretofore proposed control unit. The curve A/F represents the content of fuel in an air-fuel mixture actually supplied to the engine 30. The output voltage $V_S$ of the oxygen sensor 10 after amplification in an amplifier (amplification factor is 1:1) is put into a comparator for comparison with a reference voltage which is either a constant voltage signal $V_C$ or a two-level voltage signal that becomes a relatively high-level signal $V_{C1}$ while a lean mixture is supplied to the engine and becomes a relatively low-level signal $V_{C2}$ while a rich mixture is supplied to the engine. The comparator outputs a voltage signal $S_F$ which becomes a high-level signal (e.g. +5 V) indicative of an air/fuel ratio below the stoichiometric ratio (i.e. rich mixture) when the output voltage $V_S$ of the oxygen sensor is above the reference voltage $V_C$ or $V_{C2}$ and which becomes a low-level signal (e.g. −5 V) indicative of an air/fuel ratio above the stoichiometric ratio (i.e. lean mixture) when $V_S$ is below $V_C$ or $V_{C1}$.

The air/fuel ratio signal $S_F$ produced in this manner is used to adjust the feed rate of fuel to the engine such that the fuel is decreased while the signal $S_F$ indicates a rich mixture but is increased while the signal $S_F$ indicates a lean mixture to thereby minimize deviations of actual air/fuel ratio in the engine from the intended stoichiometric ratio.

However, air/fuel ratios detected by this method may become inaccurate during transitional operating conditions of the engine, such as during acceleration with temporarily increased feed of fuel or during temporary cutoff of the fuel feed. Under such operating conditions there occurs a considerable rise or fall in an average level of the output voltage $V_S$ of the oxygen sensor 10, whereas the reference voltage $V_C$, or $V_{C1}$ and $V_{C2}$, remains at the fixed level. Then, there arises a possibility that a change in the actual air/fuel ratio across the stoichiometric ratio during or immediately after operation of the engine under such conditions does not cause the output voltage $V_S$ of the sensor to intersect the reference voltage $V_C$, $V_{C1}$ or $V_{C2}$, so that the air/fuel ratio is misjudged. The present invention has an object of solving such problem in the air/fuel ratio detection method illustrated in FIG. 4.

Figure 5:
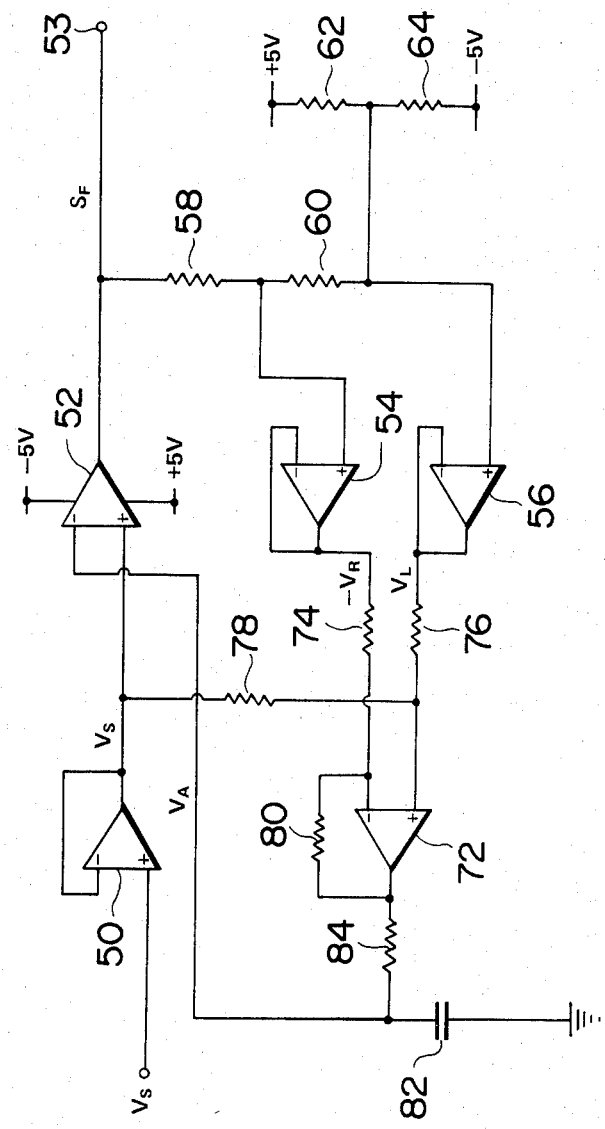
FIG. 5 is a circuit diagram showing an air/fuel ratio monitoring embodying the present invention.

FIG. 5 shows an air/fuel ratio monitoring circuit embodying the present invention, as a primary part of the control unit 40 in FIG. 2. In this circuit the output voltage $V_S$ of the oxygen sensor 10 in FIG. 2 is put into a comparator 52 via an amplifier 50 preferably having an amplification factor of 1:1. The comparator 52 receives a reference voltage signal $V_A$, which is produced in this circuit in a manner described hereinafter, and outputs an air/fuel ratio signal $S_F$ based on the result of comparing the sensor output voltage $V_S$ with the reference voltage $V_A$. The air/fuel ratio signal $S_F$ is a two-level voltage signal which varies between a high-level signal (e.g. +5 V) indicative of the feed of a fuel-rich mixture to the engine 30 when $V_S > V_A$ and a low-level signal (e.g. −5 V) indicative of the feed of a lean mixture to the engine when $V_S < V_A$. Indicated at 53 is an output terminal to transmit the air/fuel ratio signal $S_F$ to another part of the control unit 40 for producing a control signal to be supplied to the element 42 of the fuel-supplying apparatus 36 in FIG. 2.

The circuit of FIG. 5 includes two amplifiers 54 and 56 and resistors 58, 60, 62 and 64 to produce two different but fixed voltages $-V_R$ and $V_L$, which are used in producing the aforementioned reference voltage $V_A$, by utilizing the air/fuel ratio signal $S_F$. The air/fuel ratio signal $S_F$ is inputed to the amplifier 54 via the resistor 58 and also to the amplifier 56 via the resistors 58 and 60. When the air/fuel ratio signal $S_F$ is the aforementioned high-level signal indicative of feeding a rich mixture to the engine the amplifier 54 puts out a fixed voltage $-V_R$, and when the air/fuel ratio signal $S_F$ is the low-level signal indicative of feeding a lean mixture the amplifier 56 puts out another fixed voltage $V_L$. The absolute value of the voltage $-V_R$ is nearly equal to the absolute value of the voltage $V_L$.

The outputs of the two amplifiers 54 and 56, are fed to an adder circuit which comprises a feedback amplifier 72 and resistors 74, 76 and 78. The output voltage $-V_R$ of the amplifier 54 is fed to a negative input terminal of the feedback amplifier 72 via the resistor 74, and the output voltage $V_L$ of the amplifier 56 is fed to a positive input terminal of the feedback amplifier 72 via the resistor 76. In addition, the sensor output voltage $V_S$, after passing through, the amplifier 50 is fed to a positive input terminal of the feedback amplifier 72 via the resistor 78. The output of amplifier 72 is fed back to the negative input terminal via a feedback resistor 80. Accordingly the output of the feedback amplifier 72 represents the addition of either the negative voltage $-V_R$ or the positive voltage $V_L$ to the sensor output voltage $V_S$. That is, the output of the adder circuit has a voltage level $V_S - V_R$ whenever the air/fuel ratio signal $S_F$ is a high-level signal indicative of a fuel-rich mixture but has a voltage level $V_S + V_L$ whenever the air/fuel ratio signal $S_F$ is a low-level signal indicative of a lean mixture.

Figure 6:
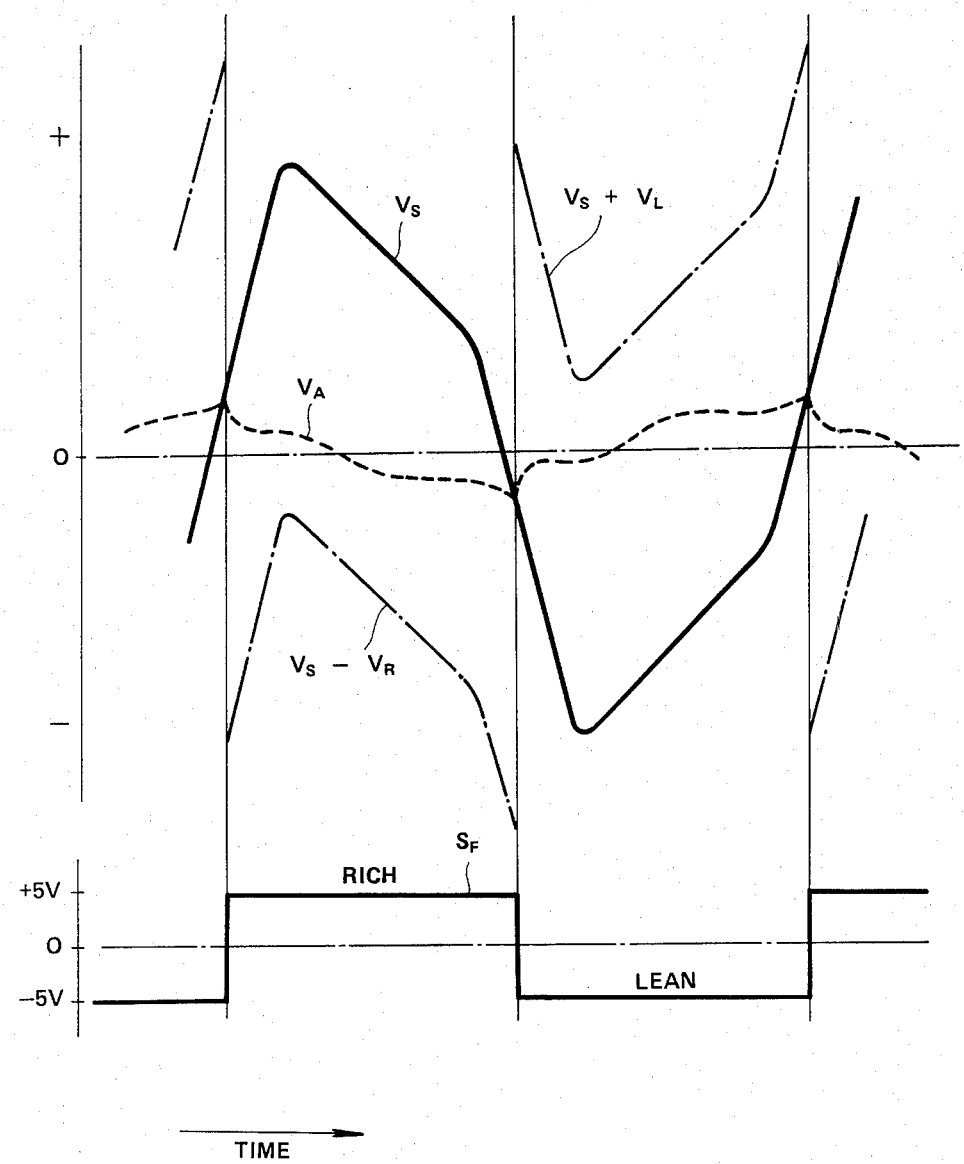
FIGS. 6–8 are charts showing the manner of function of the air/fuel ratio monitoring system of FIG. 5.

The output of the feedback amplifier 72, $V_S - V_R$ or $V_S + V_L$, charges a capacitor 82 through a resistor 84. This capacitor 82 serves the function of smoothing the voltage $V_S - V_R$ or $V_S + V_L$ to a voltage $V_A$ which slowly varies according to the sensor output voltage $V_S$ as can be seen in FIG. 6. The smoothed voltage $V_A$ is supplied to the comparator 52 as the reference voltage with which the sensor output voltage $V_S$ is compared. As mentioned hereinbefore and as shown in FIG. 6, the air/fuel ratio signal $S_F$ as the output of the comparator 52 becomes a high-level signal (indicative of a rich mixture) while the sensor output voltage $V_S$ is above the reference voltage $V_A$ and becomes a low-level signal (indicative of a lean mixture) while $V_S$ is below $V_A$.

Figure 7:
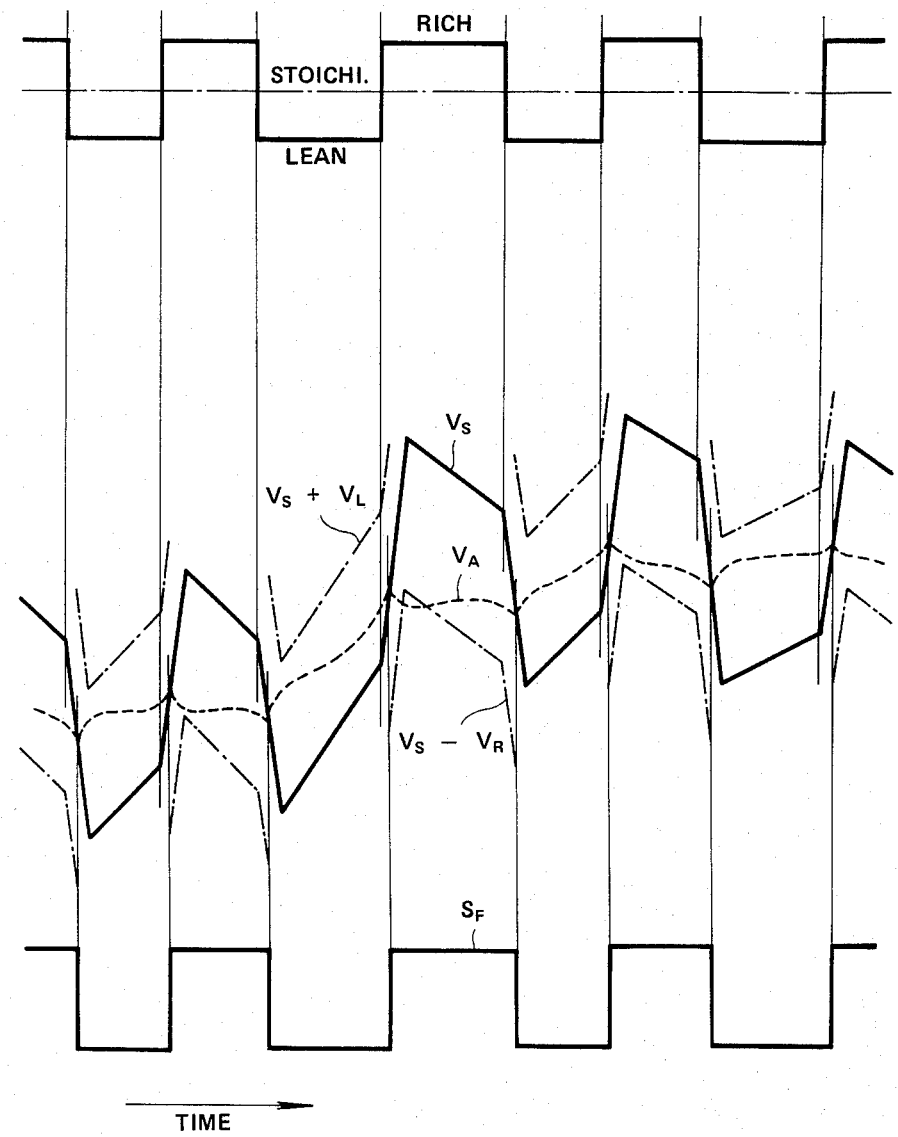

Referring to FIG. 7, when an average air/fuel ratio in the engine deviates from the stoichiometric towards the rich side by reason of the operation of the engine under transitional operating conditions, for example, when the air/fuel ratio under the feedback control continues to periodically change across the stoichiometric ratio (under such conditions the duration of each substoichiometric period will differ from the duration of the preceding or subsequent superstoichiometric period), the high-level and/or the low-level of the sensor output voltage $V_S$ will considerably vary in absolute value. Then the reference voltage $V_A$ produced and used in the air/fuel ratio monitoring circuit of FIG. 5 varies to become higher or lower as the level of the sensor output voltage $V_S$ becomes higher or lower since this reference voltage $V_A$ is produced fundamentally by adding a definite voltage to, or subtracting a definite voltage from, the sensor output voltage $V_S$. Therefore, the air/fuel ratio signal $S_F$ produced by a comparison between the sensor output voltage $V_S$ and this reference voltage $V_A$ accurately indicates whether the actual air/fuel ratio in the engine is above or below the intended stoichiometric ratio irrespective of the operating conditions of the engine.

Figure 8:
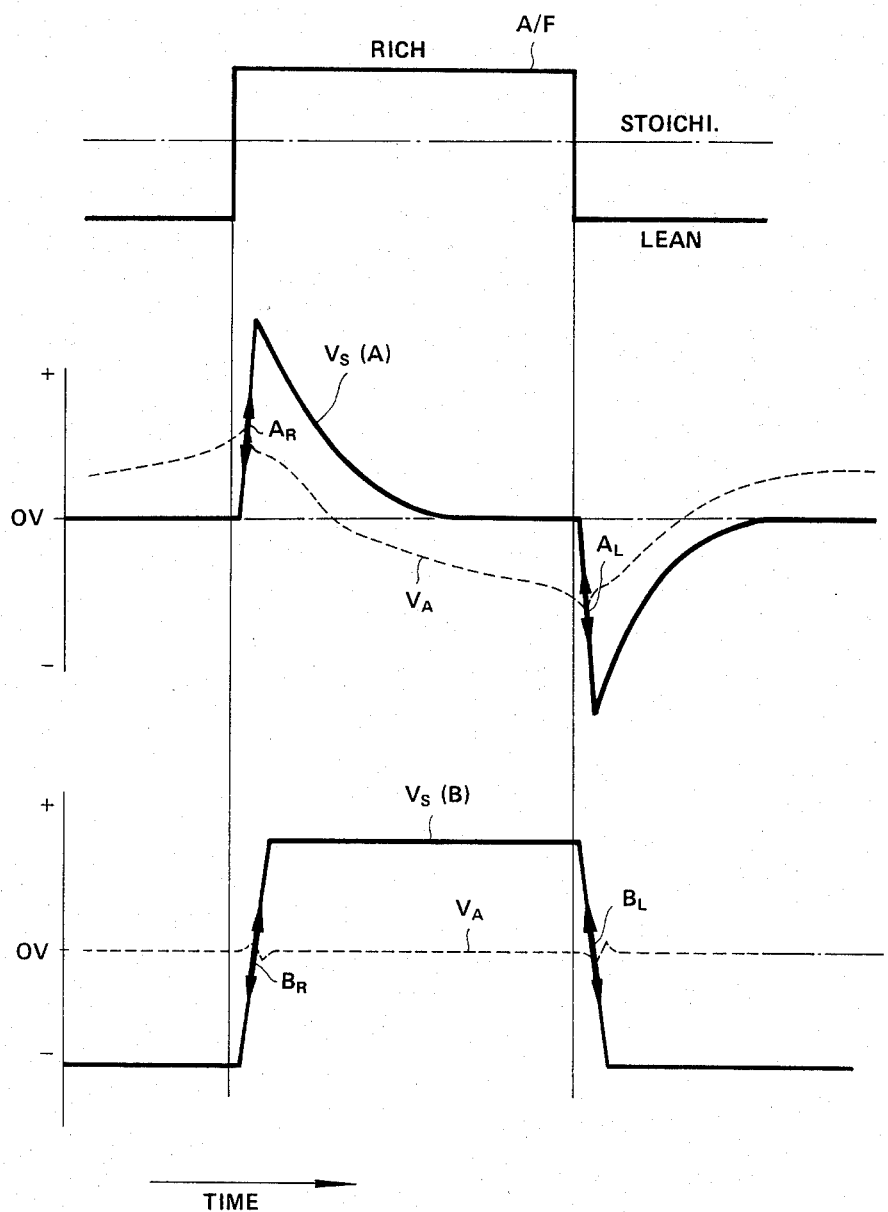

The air/fuel ratio monitoring method according to the invention has an additional advantage, which will be explained with reference to FIG. 8.

In the oxygen sensor 10 of FIG. 1, the rate of diffusion of the exhaust gas or oxygen molecules through the solid electrolyte layer 16 will vary depending on the porosity of the solid electrolyte layer 16 and also on the temperature of the solid electrolyte 16. Where the rate of gas diffusion in the solid electrolyte layer 16 is relatively high, the output voltage $V_S$ of the oxygen sensor rapidly shifts to the zero-voltage level from the high- or low-level resulting from a change in the air/fuel ratio across the stoichiometric ratio, as represented by curve $V_S(A)$ in FIG. 8. Such a sensor output voltage is commonly called a differential type output characteristic. Where the rate of gas diffusion in the solid electrolyte is very low, the sensor output voltage $V_S$ remains almost unchanged at a maximally high or minimally low level while the air/fuel ratio is below or above the stoichiometric ratio, as represented by curve $V_S(B)$ in FIG. 8. Such a sensor output voltage is commonly called an integral type output characteristic. Since the temperature of the oxygen sensor and the operating conditions of the engine affect the rate of gas diffusion in the solid electrolyte layer 16, the output characteristic of each individual oxygen sensor 10 will possibly vary from one of the two types $V_S(A)$ and $V_S(B)$ in FIG. 8 to the other or to an intermediate type.

To achieve accurate feedback control of the air/fuel ratio, it is desirable to make a comparison between the sensor output voltage $V_S$ and the reference voltage $V_A$ without a long delay from a change in the actual air/fuel ratio across the stoichiometric ratio. In other words, it is desirable that the curve $V_S(A)$ or $V_S(B)$ of the sensor output voltage $V_S$ intersects the curve of the reference voltage $V_A$ in regions $A_R$ and $A_L$ or in regions $B_R$ and $B_L$ as indicated by arrows in FIG. 8. The present invention can satisfy this desire whether the output characteristic of the oxygen sensor is of the differential type or of the integral type, because the reference voltage $V_A$ is variably determined on the basis of the sensor output voltage $V_S$.

Figure 9:
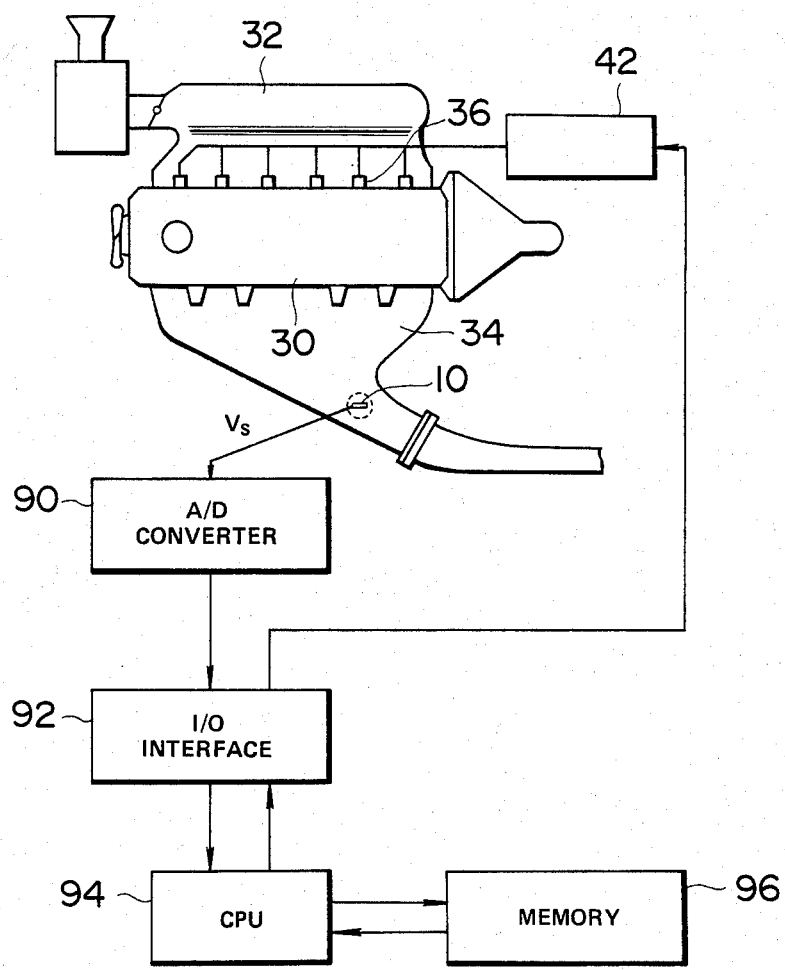
FIG. 9 is a diagrammatic presentation of an internal combustion engine system including a digital air/fuel ratio monitoring system of according to the invention.
Figure 10:
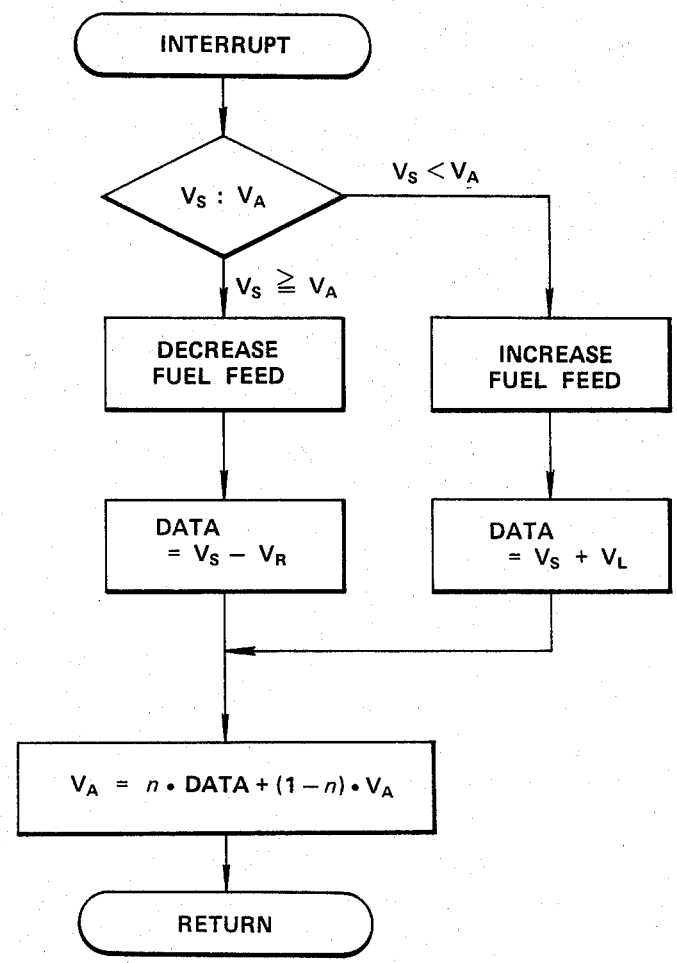
FIG. 10 is a flow chart showing the function of the air/fuel ratio monitoring system in FIG. 9.

Referring to FIGS. 9 and 10, a digital circuit is illustrated which uses a microcomputer and serves substantially the same function as the analog circuit of FIG. 5.

In FIG. 9, the output voltage $V_S$ of the oxygen sensor 10 disposed in the exhaust passage or exhaust manifold 34 of the engine 30 is converted into a digital signal in an analog-to-digital converter 90 and put into a central processing unit 94 of a microcomputer through an input-output interface 92. The CPU 94 executes a series of commands preprogrammed in a memory unit 96 to determine the value of the reference voltage $V_A$ and to make a judgement from the relation between the sensor output voltage $V_S$ and the reference voltage $V_A$ whether the actual air/fuel ratio is above or below the stoichiometric ratio. The flow chart of FIG. 10 shows the operation of the CPU 94 more particularly. In the flow chart, n represents a constant greater than 0 but smaller than 1. The routine of FIG. 10 is executed periodically at predetermined time intervals or alternatively once per a predetermined number of revolutions of the engine. Based on the aforementioned judgement the CPU 94 provides a fuel feed rate control signal to the drive element 42 of the fuel supplying apparatus 36 through the I/O interface 92. Usually, the microcomputer receives additional input signals which are representative of some parameters of the operating conditions of the engine, such as the quantity of air admitted into the engine, rpm of the engine, temperature of the cooling water and the degree of opening of the throttle valve, in order to determine basic rates of fuel feed under respective operating conditions of the engine.

When such a digital circuit including a microcomputer is employed in an air/fuel ratio monitoring system according to the invention it becomes possible to repeatedly adjust the smoothed reference voltage $V_A$ in synchronism with the engine revolution, so that the frequency of feedback can be increased during high-speed operation of the engine with the effect of improving the response and tracking of the reference voltage $V_A$ to the output voltage $V_S$ of the oxygen sensor.

What is claimed is:

1. In a system for monitoring an air/fuel ratio of air-fuel mixture supplied to an internal combustion engine, the system having an oxygen sensor of the concentration cell type disposed in an exhaust passage of the engine, the oxygen sensor having a laminate comprising an inner electrode layer, a microscopically porous layer of an oxygen ion conductive solid electrolyte and an outer electrode layer exposed to an exhaust gas for producing an output which varies between a high-level voltage signal when the air/fuel ratio is below stoichiometric and a low-level voltage signal when the air/fuel ratio is above stoichiometric, and judgement means for producing an air/fuel ratio signal indicative of whether the air/fuel ratio is above or below stoichiometric by comparing the output of the oxygen sensor with a reference voltage, said judgement means comprising a modulating means for producing a modulated voltage signal by subtracting a first predetermined voltage from the output of said oxygen sensor when said air/fuel ratio signal indicates that the air/fuel ratio is below stoichiometric and by adding a second predetermined voltage to the output of said oxygen sensor when said air/fuel ratio signal indicates that the air/fuel ratio is above stoichiometric, and smoothing means for smoothing said modulated voltage signal to produce a smoothed voltage and for supplying said smoothed voltage to said judgement means as said reference voltage.

2. A system according to claim 1, wherein said judgement means varies said air/fuel ratio signal between a high-level voltage signal when the output of said oxygen sensor is above said reference voltage and a low-level voltage signal when the output of said oxygen sensor is below said reference voltage.

3. A system according to claim 2, further comprising voltage producing means for producing said first and second definite voltages by amplifying said high-level voltage signal and said low-level voltage signal of said air/fuel ratio signal, respectively.

4. A system according to claim 1, wherein said judgement means, said modulating means, and said smoothing means comprise means for treating analog signals.

5. A system according to claim 1, wherein said judgement means, said modulating means and said smoothing means comprise a digital microcomputer.

* * * * *